United States Patent
Schouenborg

(10) Patent No.: US 8,086,322 B2
(45) Date of Patent: Dec. 27, 2011

(54) METHOD AND MEANS FOR ELECTRICAL STIMULATION OF CUTANEOUS SENSORY RECEPTORS

(75) Inventor: Jens Olaf Roe Schouenborg, Lund (SE)

(73) Assignee: Meagan Medical Inc., Vancouver, WA (US)

( * ) Notice: Subject to any disclaimer, the term of this patent is extended or adjusted under 35 U.S.C. 154(b) by 568 days.

(21) Appl. No.: 11/253,936

(22) Filed: Oct. 19, 2005

(65) Prior Publication Data
US 2006/0085056 A1     Apr. 20, 2006

Related U.S. Application Data

(60) Provisional application No. 60/624,500, filed on Oct. 19, 2004.

(51) Int. Cl.
*A61N 1/00* (2006.01)
*A61B 5/04* (2006.01)

(52) U.S. Cl. ........ 607/115; 607/119; 600/372; 600/373; 600/377; 600/382; 600/386; 600/393

(58) Field of Classification Search .................. 600/372, 600/393, 373, 382, 386; 607/119, 115
See application file for complete search history.

(56) References Cited

U.S. PATENT DOCUMENTS

| | | | |
|---|---|---|---|
| 4,837,049 A * | 6/1989 | Byers et al. ........................ 216/6 |
| 4,867,166 A | 9/1989 | Axelgaard et al. ............. 128/640 |
| 4,920,968 A * | 5/1990 | Takase ........................... 600/393 |
| 4,969,468 A | 11/1990 | Byers et al. |
| 5,449,378 A * | 9/1995 | Schouenborg .................. 607/46 |
| 5,772,688 A * | 6/1998 | Muroki .............................. 607/1 |
| 5,928,144 A * | 7/1999 | Real .............................. 600/378 |
| 6,044,286 A * | 3/2000 | Ogama ......................... 600/372 |
| 6,083,253 A * | 7/2000 | Ogama ......................... 607/75 |
| 6,277,116 B1 * | 8/2001 | Utely et al. ..................... 606/42 |
| 6,609,018 B2 * | 8/2003 | Cory et al. ..................... 600/393 |
| 6,690,959 B2 * | 2/2004 | Thompson .................... 600/372 |
| 6,785,569 B2 * | 8/2004 | Schmidt et al. ............... 600/372 |
| 6,821,281 B2 * | 11/2004 | Sherman et al. .............. 606/131 |
| 6,918,907 B2 * | 7/2005 | Kelly et al. ..................... 606/41 |
| 7,212,865 B2 | 5/2007 | Cory |
| 7,457,667 B2 * | 11/2008 | Skiba .............................. 607/50 |
| 2002/0028991 A1 * | 3/2002 | Thompson .................... 600/372 |
| 2002/0120260 A1 * | 8/2002 | Morris et al. ................... 606/41 |
| 2002/0120261 A1 * | 8/2002 | Morris et al. ................... 606/41 |
| 2003/0050548 A1 | 3/2003 | Schmidt et al. ............... 600/373 |

(Continued)

FOREIGN PATENT DOCUMENTS

CA    2584722 A1    4/2006

(Continued)

OTHER PUBLICATIONS

International Search Report.

(Continued)

*Primary Examiner* — Niketa I Patel
*Assistant Examiner* — Nicole F Lavert
(74) *Attorney, Agent, or Firm* — Blank Rome LLP

(57) ABSTRACT

Electrode plate comprising a stiff or flexible electrically non-conductive plate element having a front face and a rear face and a pattern of needle-like (NL) electrodes for electrical stimulation of cutaneous thin Aδ/C fibers and conductive plate (CP) electrodes for electrical stimulation cutaneous large Aβ fibers disposed on the front face.

33 Claims, 9 Drawing Sheets

U.S. PATENT DOCUMENTS

| | | | |
|---|---|---|---|
| 2004/0164454 A1 | 8/2004 | Gartstein et al. | |
| 2004/0181216 A1* | 9/2004 | Kelly et al. | 606/41 |
| 2005/0043775 A1* | 2/2005 | John et al. | 607/69 |
| 2005/0075670 A1* | 4/2005 | Bengtsson | 607/3 |
| 2005/0203366 A1* | 9/2005 | Donoghue et al. | 600/378 |
| 2006/0047194 A1* | 3/2006 | Grigorov | 600/372 |
| 2006/0111626 A1* | 5/2006 | Rossing et al. | 600/372 |
| 2006/0149341 A1* | 7/2006 | Palti | 607/63 |
| 2006/0173261 A1* | 8/2006 | Kall et al. | 600/372 |
| 2007/0015984 A1* | 1/2007 | Yeo et al. | 600/372 |
| 2007/0106359 A1* | 5/2007 | Schaer et al. | 607/129 |
| 2007/0123766 A1* | 5/2007 | Whalen et al. | 600/395 |
| 2007/0169333 A1* | 7/2007 | Donoghue et al. | 29/592 |
| 2007/0238944 A1* | 10/2007 | Axelgaard | 600/372 |
| 2007/0265692 A1* | 11/2007 | Koop et al. | 607/119 |
| 2007/0270927 A1* | 11/2007 | Fisk | 607/119 |

FOREIGN PATENT DOCUMENTS

| | | |
|---|---|---|
| CN | 101124010 A | 2/2008 |
| EP | 0275642 | 7/1988 |
| EP | 1809370 | 10/2005 |
| HK | 1118024 A | 1/2009 |
| JP | 01164373 A * | 6/1989 |
| JP | 2008516724 T | 5/2008 |
| KR | 001127 | 11/2007 |
| WO | WO 93/23112 | 11/1993 |
| WO | WO9323112 | 11/1993 |
| WO | 2006043885 A1 | 4/2006 |

OTHER PUBLICATIONS

First Office Action in related Chinese Patent Application No. 200580042302.4 dated Aug. 14, 2009 (16 pgs) with English translation.

* cited by examiner

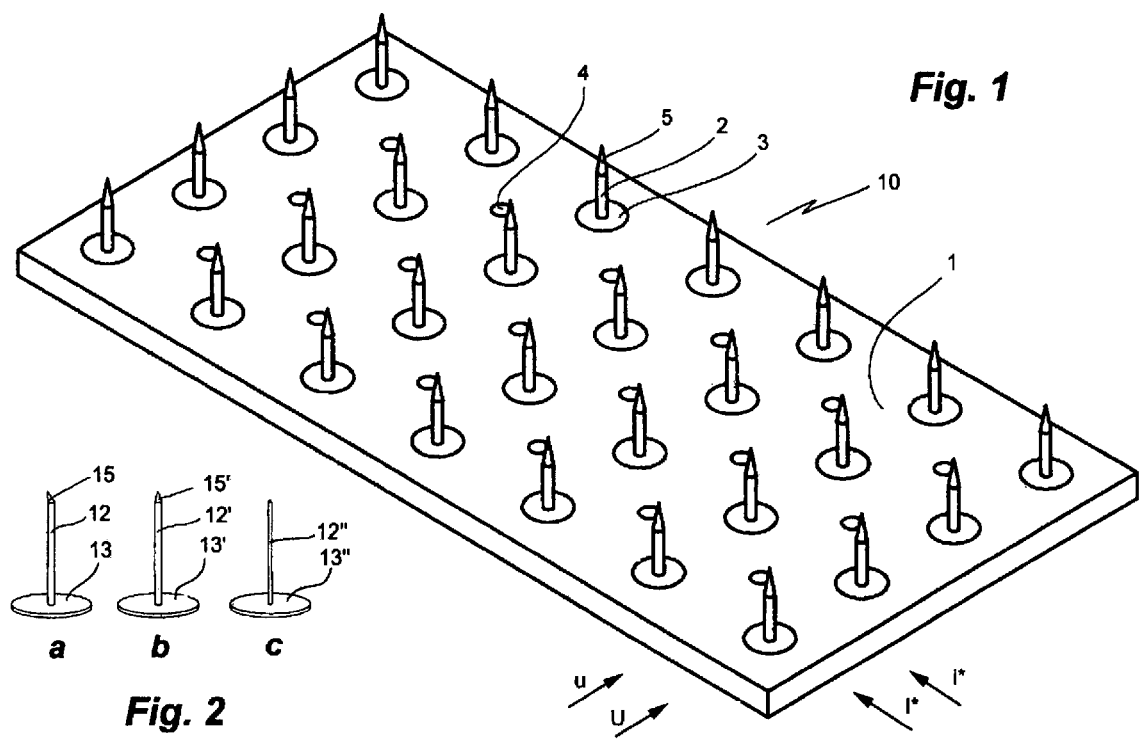

METHOD AND MEANS FOR ELECTRICAL STIMULATION OF CUTANEOUS SENSORY RECEPTORS

CROSS-REFERENCE TO RELATED APPLICATION

This application claims the benefit of U.S. Provisional Application No. 60/624,500 filed Oct. 19, 2005, which is incorporated herein by reference.

FIELD OF THE INVENTION

The invention relates to an electrode plate for electrical stimulation of cutaneous sensory receptors, in particular for patterned stimulation of cutaneous Aβ fibers and cutaneous Aδ/C fibers within defined skin areas for the relief of itch, pain and other medical or animal care or cosmetic purposes, and to a corresponding use and method of treatment.

BACKGROUND OF THE INVENTION

In the skin, different sensory qualities interact competitively with one another (Schmidt R F (1971). Presynaptic inhibition in the vertebrate central nervous system. *Ergebn. Physiol.* 63:20-101; Melzack R et al. (1965). Pain mechanisms: a new theory. A gate control system modulates sensory input from the skin before it evokes pain perception and response. *Science* 150: 971-979; McMahon S B et al. (1992). Itching for an explanation. *Trends in Neurosci.* 15/12:497-501; Ward L et al. (1996). A comparison of the effects of noxious and innocuous counterstimuli on experimentally induced itch and pain. *Pain* 64:129-138). Mechanical stimulation inhibits ongoing pain (Wall P D et al. (1960). Pain, itch, and vibration, *A.M.A. Archives of Neurology* 2:365-375; Sjölund B H et al. (1990). Transcutaneous and implanted electric stimulation of peripheral nerves. In: J. Bonica (ed): *Management of Pain,* $2^{nd}$ edition, Lea & Fegiber, Philadelphia, p 1852-1861)). To utilize the interactions between tactile and pain pathways, transcutaneous electrical nerve stimulation (TENS) was developed in the seventies (Flowerdew et al. (1997); Osiri et al, (2003)). This method uses surface electrodes that are attached to the skin overlying the nerve to be stimulated. Stimulation intensity is such that mainly the large nerve fibers, classified as Aβ fibers, carrying tactile information, are activated. Different forms of TENS are known and are frequently used in the clinic. Conventional TENS uses high frequency stimulation of tactile Aβ fibers. Another form of TENS was later developed to activate deep afferents from the muscles (Sjölund et al. 1990). In this case, TENS is given with a low frequency at an intensity that cause muscle contraction. Both methods have been shown to produce analgesia, although the mechanisms of action appear to be different (Sjölund et al. 1990). TENS is, however, not suitable for the stimulation of unmyelinated fibers classified as C fibers. Using TENS, the threshold current needed to activate C fibers is very high and thus cannot be tolerated. Clinical effects of TENS are summarized by Flowerdew and Goadsby (1997), Osiri et al (2003).

Particularly strong interactions are found between submodalities of the nociceptive system (here including itch), e.g. low frequency electrical stimulation of Aδ/C fibers, i.e. thin myelinated fibers and non-myelinated fibers, respectively, may cause a durable depression of nociceptive C fiber transmission both in vivo (Sjölund B H (1985). Peripheral nerve stimulation suppression of C-fiber-evoked flexion reflex in rats. Part 1: parameters of continuous stimulation. *J. Neurosurg.* 63:612-616; Sjölund B H (1988). Peripheral nerve stimulation suppression of C-fiber-evoked flexion reflex in rats. Part 2: parameters of low-rate train stimulation of skin and muscle afferent nerves. *J. Neurosurg.* 68:279-283; Klein T et al. (2004). Perceptual correlates of nociceptive long-term potentiation and long-term depression in humans. *J. Neurosci.* 24:964-71) and in vitro spinal preparations (Sandkühler et al., 1997). Furthermore, noxious mechanical stimulation that strongly activates tactile Aβ and nociceptive C fibers, such as scratching, reduces itch. These interactions occur at several levels in the somatosensory system, e.g. the dorsal horn of the spinal cord (Melzack et al. (1965); Cervero F et al. (1979). An electrophysiological study of neurones in the substantia gelatinosa rolandi of the cat's spinal cord. *Quart. J. Exp. Physiol.* 64:297-314) and the thalamus (Olausson B et al. (1994). Dorsal column inhibition of nociceptive thalamic cells mediated by gamma-aminobutyric acid mechanisms in the cat. *Acta Physiol. Scand.* 152: 239-247.), and are often topographically well organized. It is therefore important to stimulate local areas that are related to the itchy or painful body part.

To enable stimulation of thin afferent fibers, including Aδ and C fibers for the relief of itch and pain, a new technique, termed Cutaneous Field Stimulation (CFS), was introduced (Schouenborg, 1995; Nilsson et al, 1997, Nilsson and Schouenborg, 1999; Nilsson et al, 2003, 2004). CFS allows topographically restricted and tolerable electrical stimulation of thin (Aδ and C) cutaneous fibers but is not useful for the stimulation of Aβ fibers. CFS uses a flexible rubber plate with multi-array needle-like electrodes regularly fixed at 2-cm intervals. Each electrode is surrounded by an elevated "stop-device" about 2.0 mm in diameter that protrudes 2.0 mm from the plate. The electrode tip usually protrudes 0.3 mm from the stop-device. When gently pressing the electrode plate against the skin, the electrode tips are introduced close to the receptors in the epidermis and the superficial part of dermis (Kruger et al, 1985). Since the electrodes traverse the electrically isolating horny layer of the epidermis and the current density is high near the sharp electrode tips, the voltage and current required for stimulating cutaneous nerve fibers are small, typically less than 10 V and up to 0.8 mA, respectively. As the current density decreases rapidly with distance, localized stimulation is achieved. The electrodes are stimulated consecutively with a constant current stimulator, each electrode with a frequency of 1-10 Hz (pulse duration 1.0 ms) and treatment duration of 5-45 min. A self-adhesive surface (TENS) electrode serves as anode and is usually placed about 5-30 cm away from the needle electrode plate. Clinical effects of CFS have been summarized by Nilsson et al., 2004.

Arrays of needles on stiff electrode plates are known in the art. In these cases there are no means of controlling skin indentation other than the length of the needles. Due to the fact that most body parts are curved; such electrode plates usually do not allow controlled skin penetration of multiple needle electrodes to a defined skin depth.

Shortcomings of the Present Technology

1. Given the strong interactions between different sensory modalities and the strong effects of Aδ/C fibers it would be a considerable advantage to combine effective Aβ fiber stimulation (such as TENS) and Aδ/C fiber stimulation (such as CFS) in the same equipment. Then the aversiveness of Aδ/C fiber stimulation could be masked by concurrent A/β fiber stimulation. There is, however, no known method that combines an effective stimulation of Aβ fibers at multiple plates and in a tolerable way, with consecutive stimulation of Aδ/C fibers with a pattern of needle-like electrodes within a defined skin area. Moreover, there is no known method to combine TENS and CFS in one treatment.

2. During the onset of CFS, a pricking pain sensation is elicited. While being tolerable it is initially uncomfortable and this may reduce compliance in children and persons with sensitive skin. Existing techniques have no solution to this problem other than a gradual increase in stimulation intensity.

3. Known devices for cutaneous Aδ/C fiber stimulation are not easily applied to the skin. For example, the CFS technique utilizes a bandage to attach the electrode plate to the skin. In some situations this is impractical and thus reduces patient compliance. A method that enables easy attachment of the electrode ensemble and that at the same time keep the electrode tips at a defined depth in the skin without taking recourse to a bandage would be a considerable improvement.

4. Known methods for multi-channel electrode stimulation of Aδ/C fibers use an electrode plate that does not allow moisture from the skin area covered by the plate to evaporate. This results in accumulation of moisture between the plate and the skin. This can short-circuit the electric pulses between the active electrodes and the reference electrode. Furthermore, it prevents long-term use of the electrode plate under, for instance, a plaster of Paris. Since the skin often becomes very itchy under a plaster of Paris, this is an obvious shortcoming.

5. Electrodes known in the art protruding from the CFS plate as disclosed in WO 93/23112, granted to European Patent No. 1993910490 on Aug. 14, 1996, are made of a conducting material that is different from that of the stop device that surrounds the electrode. This arrangement decreases the precision with which the length of the protruding electrode tips are made during manufacture. As is it important to control the depth in the skin, this is a clear disadvantage.

OBJECTS OF THE INVENTION

It is an object of the invention to remedy at least some of the aforementioned shortcomings.

In particular, it is an object of the invention to provide a method of consecutively stimulating Aβ fibers and Aδ/C fibers in an efficient manner and over a large skin area.

A further object of the invention is to provide a means for such stimulation.

Further objects of the invention will become obvious from the study of the following summary of the invention, a number of figures illustrating preferred embodiments thereof, and the appended claims.

SUMMARY OF THE INVENTION

The combination of cutaneous Aδ/C and Aβ fiber stimulation is known to effectively alleviate pain and itch. Due to interactions between tactile and nociceptive pathways in the central nervous system, the combined stimulation of cutaneous Aδ/C and Aβ fibers makes the stimulation treatment tolerable. The present invention provides a method and a means incorporating this important principle. The means of the present invention providing the aforementioned combined stimulation is an electrode plate carrying two kinds of electrodes, one termed needle-like (NL) electrodes for intracutaneous stimulation of cutaneous thin Aδ/C fibers, the other termed conductive plate (CP) electrodes for transcutaneous stimulation of cutaneous large Aβ fibers. The electrode plate can be easily attached to the skin. In this application the face of the plate that abuts the skin in an attached position is termed front face, whereas the face opposite thereto is termed rear face. The NL and CP electrodes are mounted in a pattern, in particular in an array, on the front face of the electrode plate from which they rise about perpendicularly. It is preferred for the CP electrodes to be arranged in close proximity to the NL electrodes, in particular in a manner so to make the average distance of the two to four CP electrodes most closely disposed around an NL electrode to that NL electrode substantially shorter than the corresponding distance of the two to four most closely disposed neighboring NL electrodes, in particular shorter by 50% or 75% or more. In a preferred embodiment the electrode plate is designed so as to allow moisture to evaporate from the skin in an attached position. A preferred array is the arrangement of CP electrodes in two rows or more, each row comprising three or more CP electrodes preferably disposed equidistantly, each pair of rows being interspaced by a row of NL electrodes preferably disposed equidistantly. The pattern of CP and NL electrodes may also be irregular such as, for instance, in a manner of the pattern density decreasing in the direction of its periphery. A preferred horizontal distance between a CP electrode and a neighboring NL electrode is from 1 to 20 mm, more preferred from 5 to 20 mm. It is preferred for NL electrodes to have a skin penetration capability of from 0.1 mm, more preferred from 0.2 or 0.3, to 10 mm or more.

The electrode plate of the invention is preferably flexible so as to allow it to be bent. The entire electrode plate need not be flexible but only portions of it, in particular portions disposed between rows of CP and NL electrodes. The thickness of the electrode plate of the invention is generally small in comparison with the extension of its front and rear faces, such as from 1:3 to 1:10 and even 1:15 and more. In addition to being flexible the electrode plate preferably comprises resiliently extendable and/or compressible sections, in particular in portions disposed between rows of CP and NL electrodes. Suitably the backbone of the electrode plate of the invention, also termed "electrode plate element" in the following, is of or comprises a polymer material such as polyurethane, polyester or polycarbonate. Alternatively or additionally, it may comprise or consist of a non-woven or woven material, such as medical plaster.

According to a preferred aspect of the invention the electrode plate comprise shallow depressions, such as indents, groves, dimples, channels and similar, in which CP electrodes and an adhesive means for keeping the electrode plate in abutment with the skin area are provided, preferably equidistantly spaced columns of CP electrodes. It is preferred for wall portions of the depressions extending in a skew direction in respect of the main plane of the generally flat plate to be flexible and even resilient, in particular more flexible and optionally resilient than wall portions on which the electrodes are mounted and/or wall portions disposed between electrodes of the same kind, that is, in an electrode row.

The aforementioned features allow the electrode plate to be secured on the part of the body on which it is disposed without having to take recourse to conventional fastening means such as bandages, ribbons, adhesive bands or similar fastened to the rear face of the electrode plate and/or at its circumference.

According to another preferred aspect of the invention the electrode plate is provided with elevations, such as ridges, calottes, hemispheres, cones, such as cones with rounded tops, and similar disposed between the depressions. On these elevations the NL electrodes are disposed so as to protrude therefrom in a direction substantially perpendicular to the general plane of the electrode plate and thus about perpendicularly to the skin area to which the electrode plate is intended to be applied. This provides for their optimal contact with the skin. Preferably the elevations are demarcated from the remainder of the electrode plate surface so as to cause a focused pressure on the elevations when the electrode plate is in a position attached to the skin. That pressure makes the NL electrodes penetrate to a desired depth, preferably corresponding to the length by which the NL electrodes extend from the electrode plate. The CP electrodes are disposed in-between the elevations, such as in depressions of the aforementioned kind, with the proviso that they are arranged in close proximity of the NL electrodes.

An electrode plate element of the invention thus may have a wavy form such as that of corrugated sheet. It is immaterial whether the valleys in the sheet are considered to be depressions or the crests to be elevations, the important feature being that the NL electrodes are disposed on portions of the plate element that, if the plate element is applied to the skin, are the first touching the skin, whereas the CP electrodes are disposed on portions of the plate element that will only contact the skin after application of pressure to the face opposite of the face on which they are disposed.

The design of the flexible conductive plate of the invention with its uneven surface provided with adhesive means in depressions of its front face ensures that a desired skin penetration of the NL electrodes is maintained also after the external pressure applied to the back face is released at the end of mounting. The front face of the conductive flexible electrode plate of the invention is temporarily flattened when the plate is applied to the skin by making it abut the skin and applying pressure to its rear face, preferably by first making it abut the skin along one of its edges or, if the plate has a circular or oval configuration, at one point of its circumference, and then "rolling" it out on the skin while applying and maintaining pressure to the portions that are consecutively abutting the skin. When the pressure on its rear face is released, the electrode plate seeks to assume its original conformation, thereby making the skin at least partially follow its changes in conformation and the electrode plate thereby be held in a tensioned state. The tension created in the electrode plate and the skin portion to which it is applied keeps the electrode wall portions surrounding the base of the NL electrodes pressed against positions and, thereby, the NL electrodes themselves. Because of its flexible and optionally resilient nature the electrode plate can also be applied to substantially non-flat skin areas, such as the human face or a shoulder, elbow or knee.

According to a further preferred aspect of the invention the adhesive means is an electrically conductive adhesive in contact with the CP electrodes. Alternatively the CP electrodes and a conductive or non-conductive adhesive occupy different portions of depressions in the front face of the electrode plate. In such case, the adhesive is used primarily or exclusively for attaching the electrode plate to the skin.

According to still another preferred aspect of the invention, the electrode plate is provided with one or more reference electrodes and/or combined with such electrodes. It is preferred for the CP electrodes to function as reference electrodes for the NL electrodes. Preferably the electrically conductive adhesive is also used for attaching the one or more reference electrodes to the skin. The one or more reference electrode will usually be the anode whereas the NL electrodes are forming the cathode.

According to an additional preferred aspect of the invention the electrode plate of the invention is provided with multiple through holes or bores communicating its front face with its rear face to allow moisture to evaporate from the skin when the plate is in an applied position. Alternatively the electrode plate is made of a material with open pores.

According to a still further preferred aspect of the invention the NL and CP electrodes of the electrode plate are controlled by a multi-channel stimulator that is connected to them by electrical lines, enabling separate control of each kind of electrode and, if desired, of individual rows of electrodes, groups of electrodes other than individual rows, and even of single electrodes. In a preferred embodiment, the electrodes are stimulated consecutively, sets of neighboring plate electrodes and needle like electrodes being stimulated simultaneously followed by stimulation of other such sets, so that the arrival of the $A\beta$ fiber input overlaps in time that from $A\delta/C$ fibers in the spinal cord or, in case of stimulation of most of the head the trigeminus nucleus of the brain stem. On stimulation, various patterns of input in $A\delta/C$ fibers and $A\beta$ fibers can be obtained by programming the multi-channel stimulator unit accordingly. For example, a sensory input pattern mimicking that occurring on scratching the skin or massaging the body can be accomplished by stimulating the electrodes successively from one side of conductive plate area to the other.

By using a relatively high stimulation current at the plate electrodes, muscle afferents can be stimulated. Hence, the electrode plate of the invention can also be used for combined stimulation of afferent nerves from deep tissue and of cutaneous $A\delta/C$ fibers. It is also possible to stimulate deep nerves by high intensity pulses and cutaneous $A\beta$ fibers by low intensity pulses administered via CP electrodes.

The NL electrodes for $A\delta/C$ fiber stimulation can have any form that provides a current density sufficient for activating the cutaneous $A\delta/C$ fibers. Preferably, thin cylindrical electrodes with a sharp pointed tip are used as NL electrodes. The NL electrodes are attached to electrically conductors like straps or wires arranged in the electrode plate or on the plate, in which case they have to be insulated; and the conductors are in turn connected to an electrical stimulator unit, such as the aforementioned multi-channel stimulator. The number of NL electrodes should be more than three, although a lesser number may suffice in certain applications. There is no upper limit to the number of electrodes, but more than hundred or two-hundred electrodes per electrode plate are rarely needed when treating a patient. Particularly preferred are NL electrodes comprising a preferably flat and preferably circular base and an oblong rotationally symmetric, in particular cylindrical, electrode element with a pointed tip or a tip that is otherwise suitable for penetration of the skin joined to the base at its other end, the electrode element being joined to the base in a perpendicular relationship. The base and the electrode element are of an electrically conducting material, preferably of the same material, such as stainless steel, silver-plated bronze, chromium clad steel. The use of non-metallic conducting materials, such as carbon or electrically conducting polymers, is also within the ambit of the invention. This kind of NL electrode provides for good control of the depth of penetration of the skin by the electrode element and for easy mounting on an electrode plate. The length of the electrode element between tip and the base is between 0.05 and 5.0 mm dependent on the condition and the skin area treated; a preferred length is about 0.3 mm. The metallic NL-electrodes of the invention may, for instance, be turned in a lathe from stainless steel blanks or made from commercially available stainless steel needles that are cut to the desired length. The NL electrodes can be adhesively attached to the electrically conductive conductors in or on the electrode plate by using commercially available electrically conductive glue (e.g., from ECOSOLDER™ brand electrically conductive glue from Amenox Microelectronics Ltd.) or by point welding or soldering. Except for at the tip, the NL electrodes are insulated to avoid current leakage. Insulation can be provided by, for instance, a thin polymer coat, such as one of a silicon polymer or polyester.

The electrode plate of the invention thus provides a means for combined local sequential (or patterned) multi-site independent stimulation of cutaneous Aβ fibers and Aβ/C fibers within the same skin area. It takes advantage of the strong interactions in CNS between different modalities to induce itch and pain relief. Due to the "masking" effect of Aβ fiber stimulation (a buzzing feel) on Aδ/C fiber input (a feel of pricking), the disclosed technique makes it possible to stimulate also sensitive skin, such as in children.

Other types of interactions are also possible, since the electrode plate of the invention allows the provision of any combination of patterned stimulation of Aβ and Aδ/C fibers in the skin or even between deep afferent nerves from e.g. muscles and cutaneous afferent fibers. For example, it is possible to combine stimulation of deep afferents with cutaneous Aδ/C fiber stimulation by increasing the strength of the stimulation of the plate electrodes. Such stimulation is of particular interest for treating musculo-skeletal pain.

It is preferred for the NL electrodes of the invention to be from 0.1 mm, more preferred from 0.2 or 0.3 mm, to 10 mm or more in length.

According to the present invention, also disclosed is a method of stimulating sensory nerves, in particular sensory nerves of the skin, comprising:

Providing a means for controlled consecutive epidermal and intracutaneous administration of electrical stimuli comprising a stimulation face provided with a pattern of CP and NL electrodes;

Mounting the stimulation face on a skin area to be treated in an abutting relationship to make the electrodes for intracutaneous administration penentrate through the epidermis and the electrodes for epidermal administration to abut the skin, electrical conducting contact of the latter with the skin being enhanced by a conducting means applied to the skin or provided with the means for controlled consecutive epidermal and intracutaneous administration;

Stimulating sensory nerves by providing repeated consecutive electrical stimuli via the electrodes to the skin area.

It is preferred for the penetration depth of the NL electrodes to be from 0.1, more preferred from 0.2 or 0.3, to 10 mm or more.

It is preferred for the mounting to comprise a step in which the means is pressed against the skin by applying a force to its face opposite to the stimulation face, thereby temporarily flattening the means and allowing portions of the skin surface to contact an adhesive provided in depressions of the stimulation face. Upon release of the pressure, the means for administration of electrical stimuli seeks to assume its original configuration, thereby increasing the pressure on the electrodes for intracutaneous administration.

The electrode plate of the invention has multiple uses, such as the activation of endogenous mechanisms that inhibit pain and itch in patients. The electrode plate enables a precise stimulation of the receptors that are related to the painful or itchy tissue; the increase of vascularisation of the skin for cosmetic purposes or speed up the healing of skin wounds;

The treatment of animals that for different reasons cannot take drugs, such as horses or dogs that participate in competitions; in research, by allowing electrical stimulation of any combination of sensory input and for studying interactions between different sensory channels in the central nervous system.

The present invention will now be explained in more detail by referring to drawings illustrating a number of preferred embodiments. In particular it should be noted that, for reasons of clarity, the NL electrodes in the drawings are not to scale and both their length and diameter are greatly exaggerated.

BRIEF DESCRIPTION OF THE DRAWINGS

FIG. 1 is first embodiment of the electrode plate of the invention, in a perspective view;

FIGS. 2a-2c are NL electrodes comprising a base, in a perspective view;

DETAILED DESCRIPTION OF THE PRESENT INVENTION

Example 1

Embodiments of the Electrode Plate of the Invention

Figure 3:
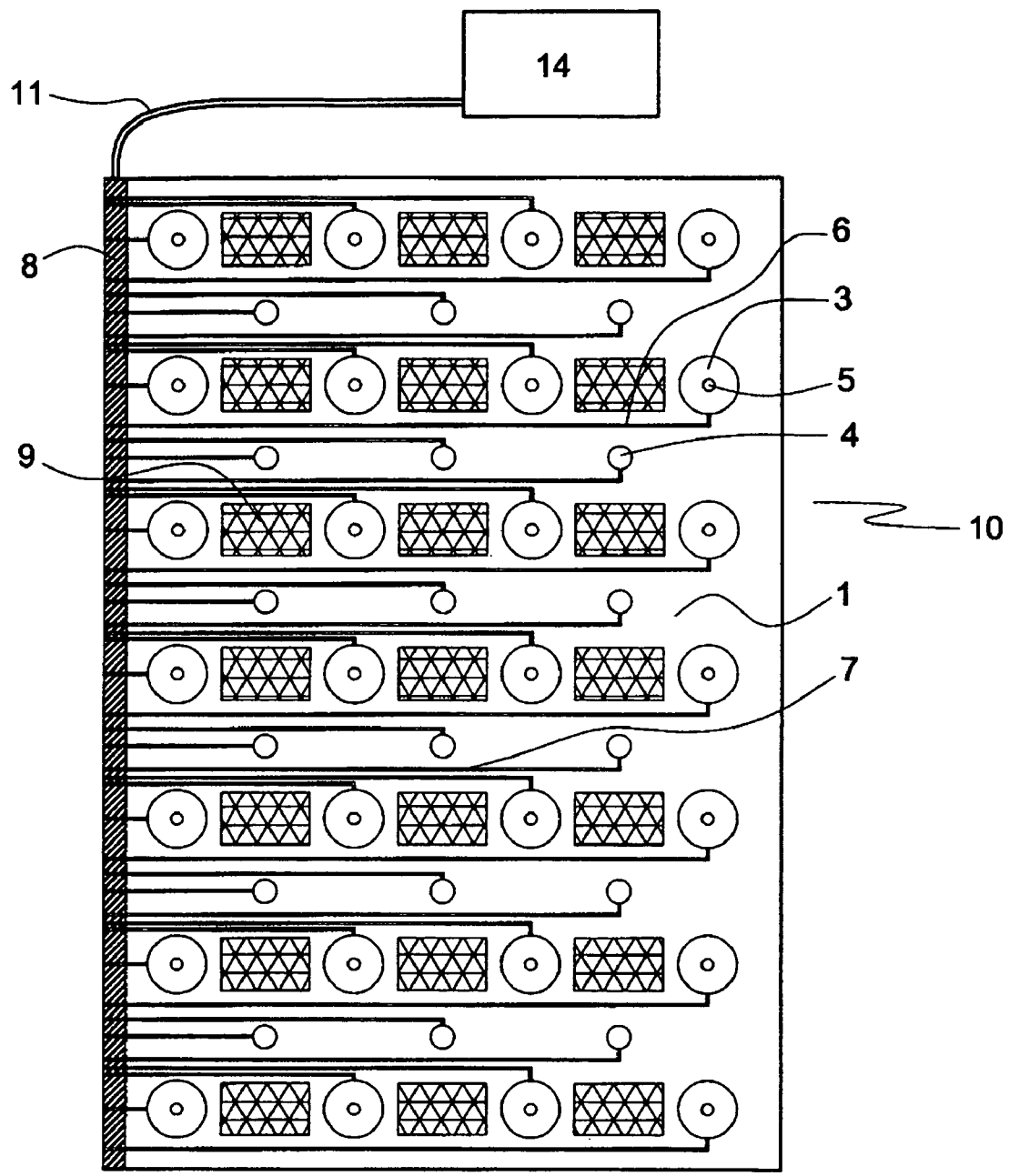
FIG. 3 is a planar view of the front face of the embodiment of FIG. 1, with a screen-printed wiring of the electrodes shown.

A first embodiment of the electrode plate of the invention is illustrated in FIGS. 1 and 3. The flat electrode plate 10 comprises a plate element 1 of a polymer material carrying, on its front face, a rectangular array of NL electrodes 2, 3, 5, each comprising a base 3 and an electrode element 2 with a pointed tip 5, and CP electrodes 4, in which rows U, etc., cf FIG. 6, four NL electrodes 2, 3, 5, are interspaced with rows u, etc., cf FIG. 6, of CP electrodes 4, each comprising three electrodes, in a manner that each CP electrode 4 is equidistant from two pairs of NL electrodes 2, 3, 5 in neighboring rows. To provide for consecutive stimulation rows or columns of NL and CP electrodes can be electrically coupled but it is equally possible to independently stimulate any desired combination of electrodes of the same kind and even each individual electrode (FIG. 3) by arranging corresponding electrical connections, such as in the form of a bunched cable 11, to a multi-channel stimulator of known kind providing controlled electrical pulses to the respective electrode or combinations of electrodes. Each NL electrode 2, 3, 5 is connected to a soldering board 8 disposed along one long side of the plate element 1 by screen-printed conductive metal bands 6 and each CP electrode 4 is connected by corresponding bands 7.

The terminal portions of the metal bands 6, 7 on the soldering board are connected via insulated copper wires (not shown) to a stimulator unit capable of individually providing each NL electrode 2, 3, 5 and each CP electrode 4 with pulsed DC current. Patches 9 of an adhesive material disposed between the NL electrodes ensure attachment of the electrode plate 10 to the skin. The electrical leads 6, 7 are insulated against the skin by a thin layer of polymer material, as are the base plates 3 and most of the electrode elements 2 except for a short portion extending from their pointed tip 5. In addition to the adhesive or instead of it, the electrode plate 10 can be fastened to a selected skin area by bandages, ribbons, plaster, etc. (not shown).

The free length, that is, the maximal depth of penetration into the skin, of the NL electrode element between its tip and its base or between its tip and the surface of the plate element bordering to it is between 0.05-5.0 mm, dependent on the condition and skin area treated. The preferred length of the needle-like electrode from tip to its base is around 0.3 mm. The NL electrodes of the invention can have any form that provides a sufficiently high electrical current density for activating the cutaneous Aδ/C fibers.

To maintain the NL electrodes fully inserted into the skin during the administration of electrical stimulation as well as for convenience, they are mounted on an electrode plate provided with clearly demarcated elevations, such as ridges and burls. The NL electrodes are mounted on top of these elevations in a manner making them protrude from the top or ridge thereof. The CP electrodes are disposed in depressions or valleys enclosed by the elevations. The depressions are provided with adhesive for adhesive connection of the electrode plate to the skin. In the process of attachment, the spatial dimensions of the electrode plate are changed. The electrode plate is flattened to make the adhesive contact the skin. The attachment of the following embodiments to the skin is based on this principle.

The difference in height between the depressions and elevations should be more than 1 mm but less than 10 mm. Smaller heights than 1 mm are useful for very small elevated areas only. The NL electrodes protrude from the elevations, which may be similar, for instance, to crests of waves, i.e., the portions of the front face that first come in contact with the skin when the electrode plate is applied. The electrode plate element can have any size and form, such as a rectangular, circular or oval form, but a size of between 10 $cm^2$ and 400 $cm^2$ is preferred. The thickness of the plate element, that is, the distance between its front and rear faces, can be different in different parts of it. For example, it is an advantage if the elevations are relatively rigid at their tips and crests where the needle-like electrodes are anchored in the electrically conductive plate and that the slopes extending from them to the valleys or depressions are or of a resilient nature.

While generally substantially flat electrode plates are best suited for application to flat skin sites, electrode plates of the invention intended for applications to non-flat body parts, such as arms, back or legs, in particular knees shoulders and elbows, may be given a form in which their front face mirrors the form of the skin area to which it shall be applied. This problem can also be solved by incorporating stretchable portions into the front wall of the electrode plate, in particular between rows of elevations and dimples.

The adhesive substance of the invention, which may be electrically conductive, is applied to the bottom of the depressions in the plate element. The adhesive strength of the adhesive substance holding the plate element attached to the skin and the resilient tension in the plate that pushes the plate away from the skin created by flattening of the electrode plate when applying it to the skin cause the elevated parts of the plate element and with them the NL electrodes to be pressed against the skin.

Figure 4:
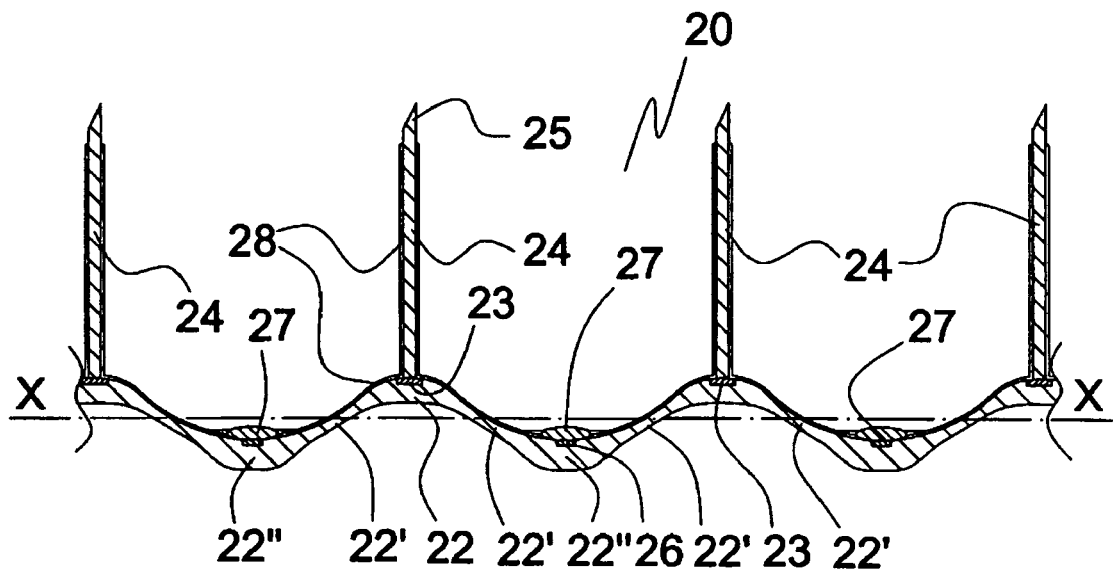
FIG. 4 is second embodiment of the electrode plate of the invention, in a non-applied state and in a section transverse to columns of NL and CP electrodes.
Figure 5:
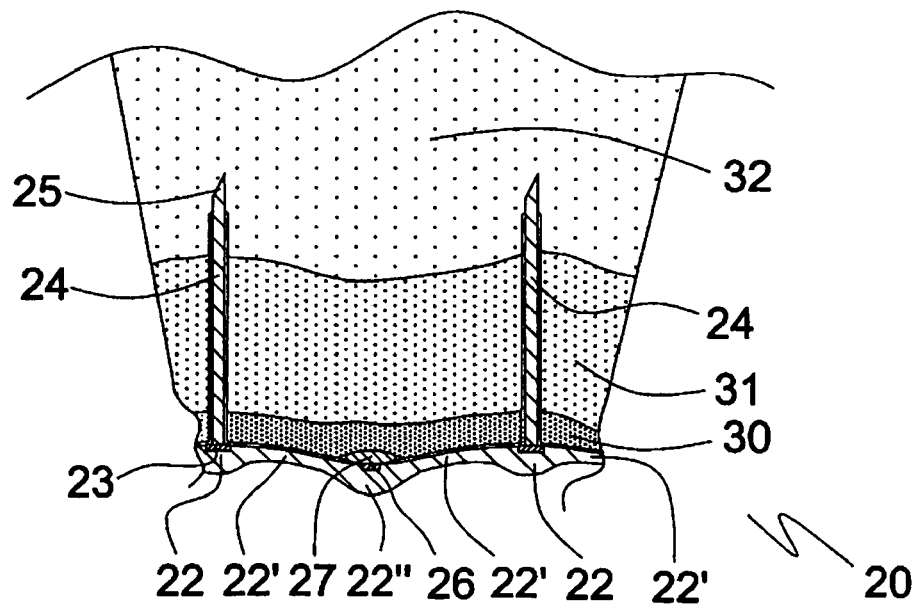
FIG. 5 is a partial view of the electrode plate of FIG. 4, in an applied state and in the same view.

A second embodiment of the electrode plate of the invention is illustrated in FIGS. 4 and 5 in a state prior to application to the skin and in an applied state, respectively. The following explanation is concerned with arrangements at the front face of the electrode plate. The electrode plate 20 comprises a wavy polymer plate element 22, 22', 22" comprising crest 22 and valley 22" portions joined by an intermediate portion 22'. First electrically conductive copper bands 23 are held in recesses in the crest portions 22. Silver-plated copper NL electrode elements 24 with a pointed tip 25 soldered to the free face of the bands 23 are disposed substantially perpendicular in respect of the general plane
X-X of the electrode plate element 22, 22', 22". Second electrically conducting copper bands 26 are held in recesses in the valley portions 22". CP electrodes 27 of an electrically conducting material that has adhesive properties are equidistantly attached to the second bands 26. A thin insulating layer 28 of polymer material is applied to the front face of the electrode plate element 22, 22', 22" except for a portion of the NL electrode elements 24 extending from their tips 25 and the front face of the CP electrodes 27. The electrode plate element 22, 22', 22" is made of a flexible and resiliently compressible/extendable material such as polyurethane or silicone rubber; the wall of its crest 22 and valley 22" portions is substantially thicker than the wall of its intermediate portion 21'. This makes bending and/or stretching and/or compression primarily occur in the intermediate portions 22'.

FIG. 5 illustrates the state of the electrode plate 20 after application to the skin. In the course of application the front face of the electrode plate element 22, 22', 22" is made to abut the skin. By gentle pressure exerted on its rear face the electrode plate element 22, 22', 22" is flattened and the NL electrode elements 24 are inserted into the epidermis 31 including the horny layer 30, and made to extend even into the dermis 32 with their sharp tip 25. By the abutting contact of the adhesive CP electrode with the skin the electrode plate 20 is firmly held in place by keeping the NL electrode elements 24 under pressure through the resilient nature of the polymer material of the electrode plate element 22, 22', 22" and thus firmly anchored in the tissue 30, 31, 32.

Figure 6:
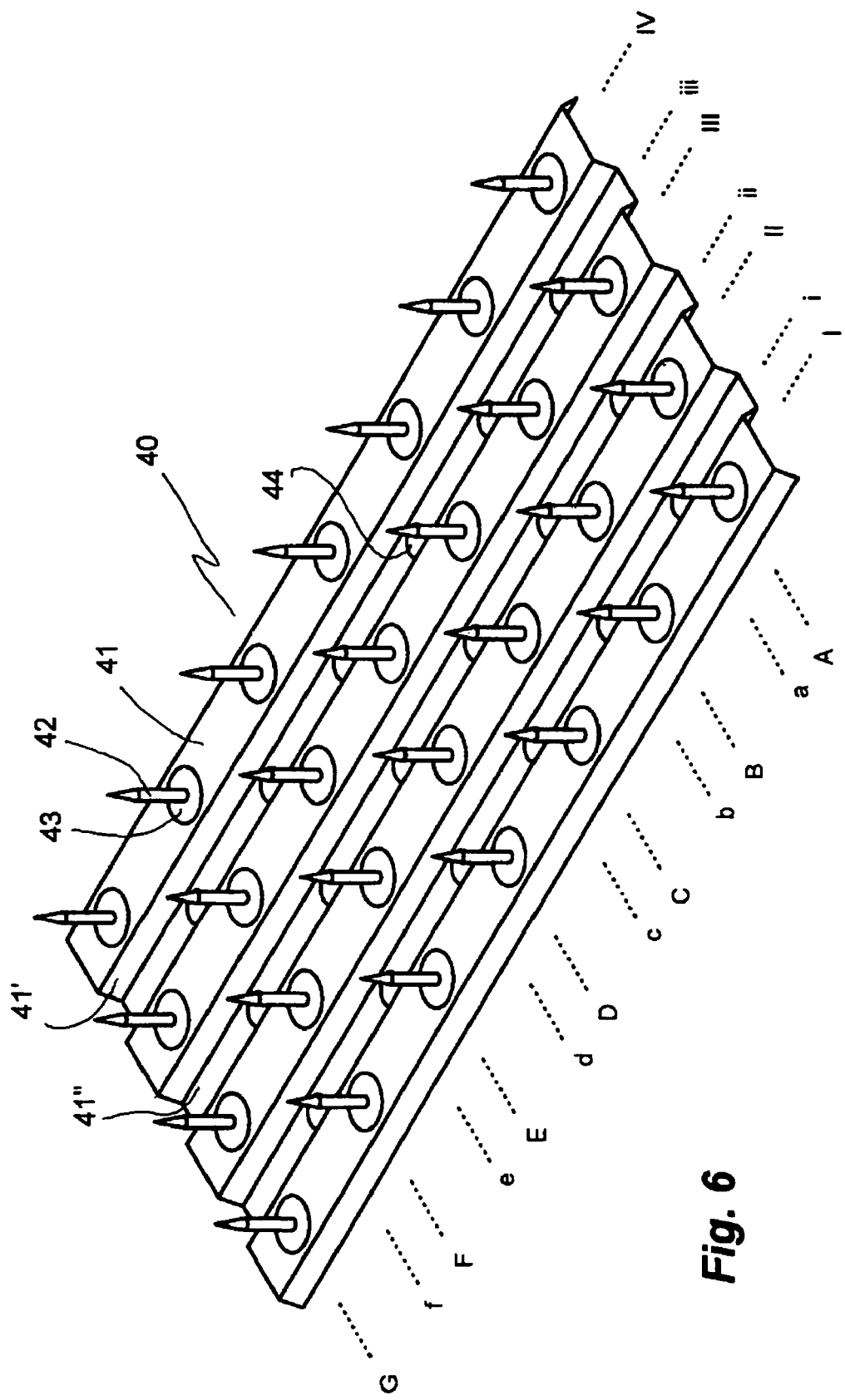
FIG. 6 is a third embodiment of the electrode plate of the invention, in a perspective view.
Figure 7:
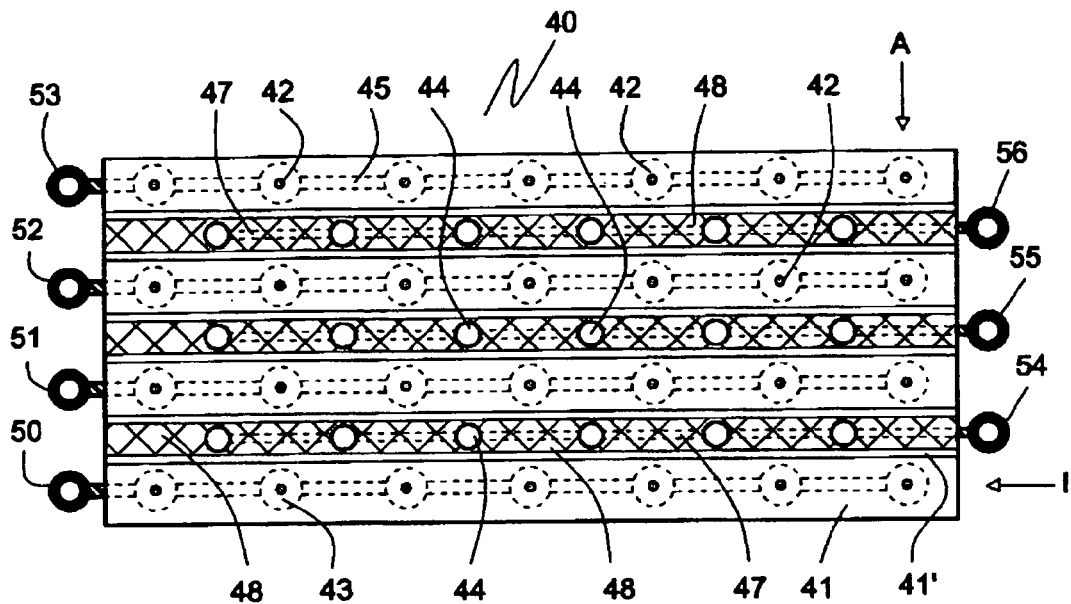
FIG. 7 is a planar view of the front face of the electrode plate of FIG. 6, with electrical wiring of columns of CP and NL electrodes shown.
Figure 8:
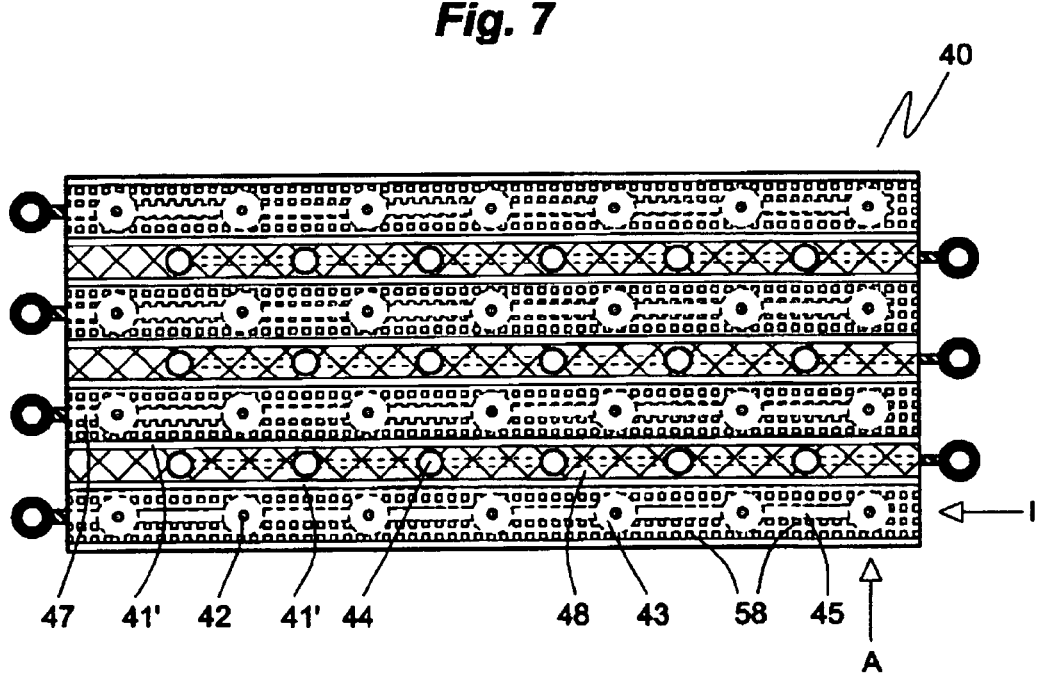
FIG. 8 is the electrode plate of FIG. 6, in the same view as in FIG. 7, provided with a pattern of venting bores.

A third embodiment of the invention is shown in FIGS. 6-8. The electrode plate element 41, 41', 41" of the electrode plate 40 is of thin and flexible but not extendable or compressible polycarbonate. Columns AI, BI, CI etc. of NL electrodes 42 mounted on a base 43 are disposed on ridge sections 41 of the plate element 40, while columns ai, bi, ci, etc. of CP electrodes 44 are disposed on bottom sections 41" of the valleys that are separated from the ridge sections 41 by side wall sections 41'. The pattern of electrode arrangement corresponds to that of FIG. 1. The plate element 41, 41', 41" can be flattened by exerting pressure on its rear face when applying it to the skin. In the flattening process the thinner side wall sections 41' will bend so as to allow the ridge sections 41 to approach the surface of the skin. The increase in distance in the flattening process between NL electrodes 42 disposed on neighboring ridge sections 41, such as, for instance, the distance between the pair of NL electrodes disposed at AI and AII, is absorbed by the resilient nature of the skin. Rolling the electrode plate 40 out on the skin by starting abutment at one of its edges will minimize this increase in distance.

FIG. 7 is a planar view of the front face of the embodiment of FIG. 6. Electrical connections 45, 47 of columns of NL electrodes 42 and CP electrodes 44, respectively, are indicated by dashed lines. The connections 45, 47 end in soldering eyes 50, 51, 52, 53 for columns I, II, etc. of NL electrodes 42 and 54, 55, 56 for columns i, ii, etc. of CP electrodes 44. The eyes 50, 51, 52, 53, 54, 55, 56 are arranged for the fixation of electrical conductors providing connection of individual columns of electrodes to a control unit (stimulator). Patches of adhesive 48 are applied to valley portions 41 adjacent to CP electrodes 44 for adhesive fixation of the electrode element 40 to the skin of a patient.

FIG. 8 is a duplicate of FIG. 7 except that a pattern of small through bores 58 communicating the front and rear sides of the electrode plate element 41, 41', 41" for venting off humidity released from the skin.

Figure 9:
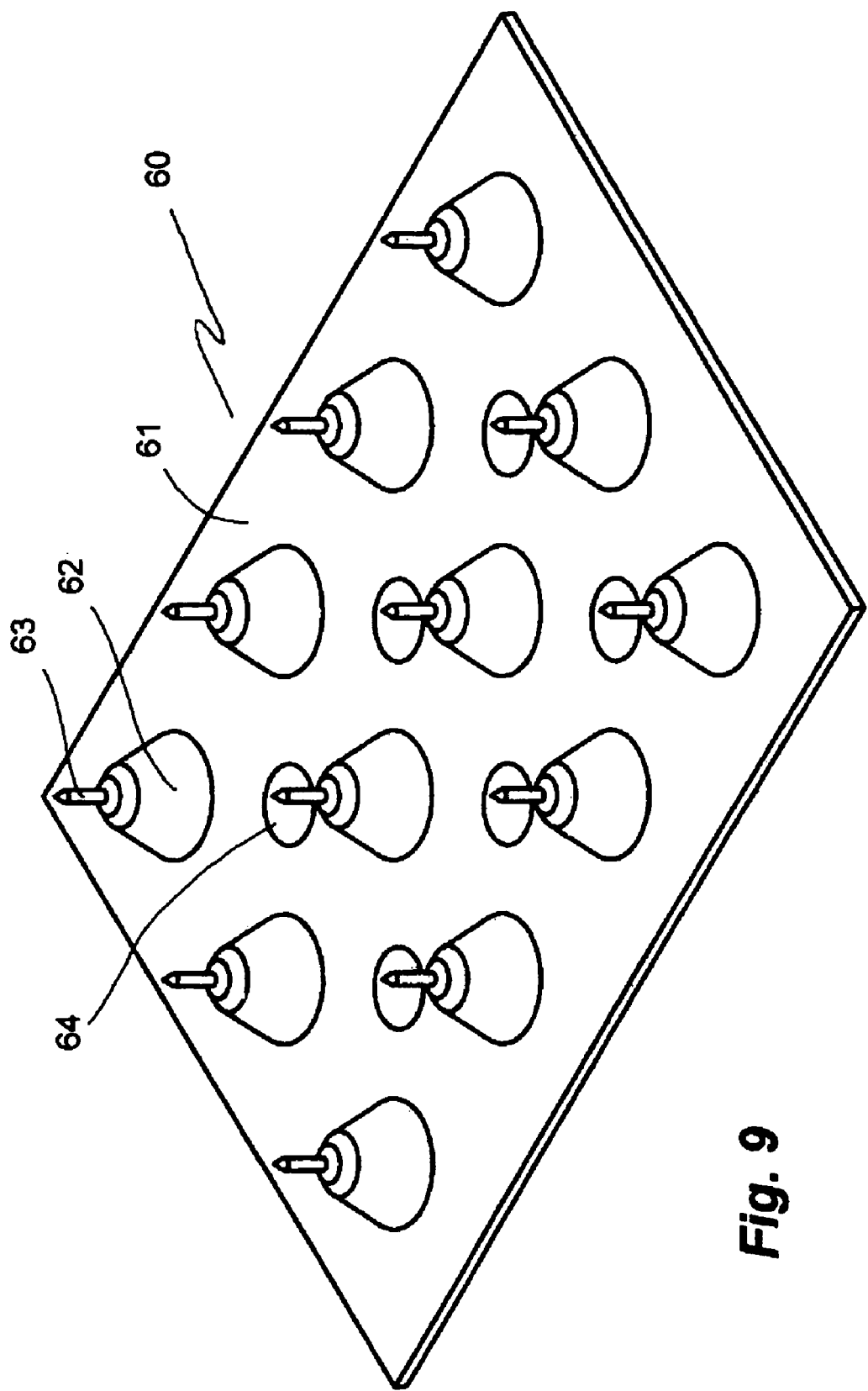
FIG. 9 is a fourth embodiment of the electrode of the invention, in a perspective view.
Figure 10:
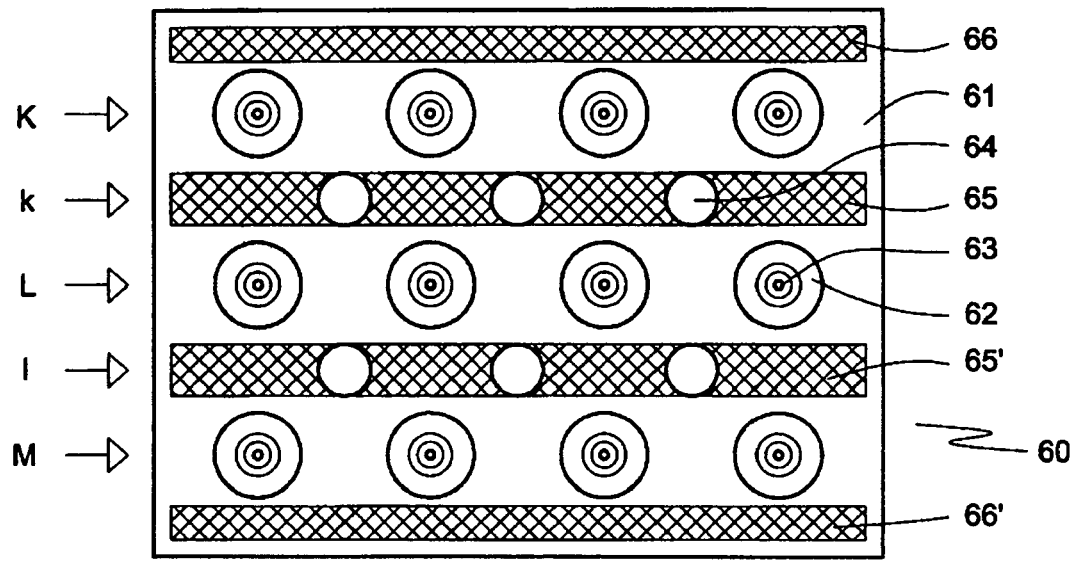
FIG. 10 is a planar view of the front face of the electrode plate of FIG. 8.

FIGS. 9 and 10 illustrate a fourth embodiment of the electrode plate 60 of the invention. A number of burls 62 is disposed on an electrode plate element 61 in a rectangular pattern of three columns K-M and four rows. One pointed NL electrode 63 is arranged on the top of each burl 62. Interspaced with the rectangular pattern or array of the NL electrodes 63 is a rectangular pattern of CP electrodes 64 of two columns k, l and three rows. Patterns of adhesive patches 65, 65'; 66, 66' arranged on the plate element 61 in-between columns of burls/NL electrodes 62, 63 and in zones disposed in-between columns of burls/NL electrodes and long edges of the plate element 61, respectively, are shown in FIG. 10.

Figure 11:
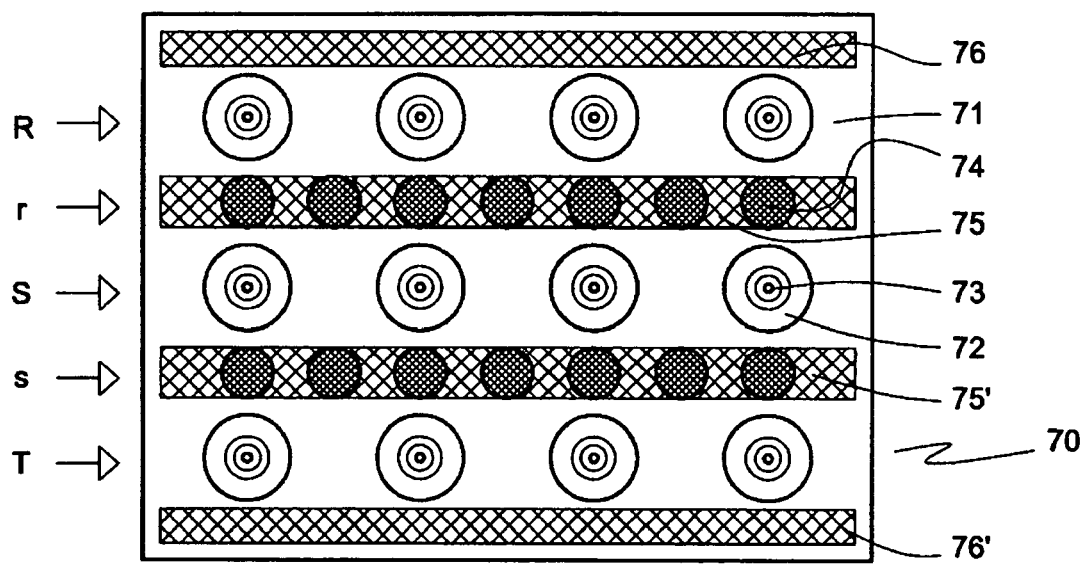
FIG. 11 is a variation of the embodiment of FIG. 8, in the same view as in FIG. 10.

The electrode plate 70 shown in FIG. 11 is a variation of that of FIGS. 9 and 10. The plate element 71 carries a substantially larger number of CP electrodes 74 per NL electrode 73 mounted on a burl 72. The CP electrodes 74 are disposed in a rectangular array of two columns r, s and seven rows; the NL electrodes 73 are disposed in a rectangular array of three columns R-T and four rows. The adhesive patches disposed between columns of burls/NL electrodes are designated 75, 75', whereas those disposed adjacent to a long edge of the plate element 71 are designated 76, 76'. For improved adhesion the CP electrodes 74 are covered with an electrically conductive adhesive.

The NL electrodes of the invention can be made from stainless steel blanks, for instance, by turning them in a lathe, but they can also be made from commercially available stainless steel needles that are cut to the desired length. The NL electrodes are attached to the electrically conductive straps or wires by using commercially available electrically conductive glue (e.g., ECOSOLDER™ brand electrically conductive glue from Amepox Microelectronics Ltd.) or by point welding or soldering, depending on the material used.

While the CP electrodes are used for local stimulation of Aβ fibers they can also serve as reference electrodes (usually coupled as anodes) for the pulses of current provided through the NL electrodes (usually coupled as cathodes). The CP electrodes can have any suitable form but need to have a sufficiently large contact area to ensure good electrical contact with the skin or the electrically conductive adhesive substance (Uni-plate Inc. USA) used in the invention of which they can be made or with which they can be covered. The electrically conductive area of the CP electrodes capable of abutting the skin or contacting the electrically conductive adhesive substance is >1 mm² but a size of >10 mm² is preferred. In an electrode plate provided with elevations for mounting the NL electrodes, such as in the electrode plates of FIGS. 6 and 9, the CP electrodes are disposed in depressions or valleys between the elevations. In this case the aforesaid conductive adhesive substance is used to both attach the electrode plate of the invention to the skin and to provide good electrical contact between CP electrodes and the skin. The conductive adhesive substance should extend over a front face area of at least 100 mm² per CP electrode. When using an electrically conductive adhesive on top of the plate electrodes, the adhesive substance covering each plate electrode should occupy an area of at least 100 mm² to ensure a good contact with the skin. Instead of or in addition to the electrically conducting adhesive an electrically non-conducting adhesive can be provided on areas of depressions not covered by the CP electrodes for securing the electrode plate on the skin.

The electrically conductive straps or wires for connecting the CP electrodes can be applied to the front face of the electrode plate by screen printing.

Electrode plate elements of a woven or non-woven material such as a medical plaster can also be used. On their front face a printed circuit optionally including CP electrodes can be provided in a single step and insulated in part or fully in a following second step. If desired, an electrode plate element of this kind can be provided with elevations of a polymer material for mounting of NL electrodes. It is also feasible to cover the entire front face of the electrode plate of the invention with an electrically conducting adhesive so as to provide one CP electrode only; the NL electrodes would then be disposed in islands not covered with adhesive.

Example II

Control of the Electrode Plate by Stimulator

In one embodiment of the invention electrically conductive straps, bonded to a thin and flexible sheet of for example polyester, are used to connect the CP and/or NL electrodes to a multi-channel stimulator. These straps are electrically insulated, by e.g. a plastic non-conductive film, except at the contact places for the electrodes and the multi-channel stimulator. In another embodiment, thin electrically conducting wires attached to the electrode plate of the invention are used to connect the CP and/or NL electrodes with a stimulator. The straps or wires are electrically insulated except at their free ends disposed at a circumferential side wall of electrode plate for easy connection with an external multi-channel stimulator (stimulating unit).

In a preferred embodiment the adhesive patches are made of electrically conductive material. The adhesive patches are then in contact with the CP electrodes on the plate which are, in turn, connected to the stimulating unit by insulated electrical conductors. In an alternative embodiment, patches of non-conductive adhesive agent disposed in the depressions are kept separate from the CP electrodes and the optional electrically conducting substance ensuring good electrical contact of the CP electrodes with the skin.

Example 3

Venting Perforations

The electrode plate of the invention of polymer material can be provided with perforations providing communication between its front and rear faces to allow moisture exuded from the skin to evaporate. Preferably from 1% to 30% of surface of the front and rear faces are covered by the perforations. Alternatively, the polymer material from which the main structure of the electrode plate is made, such as polyurethane with open pores, is permeable to water vapour.

Example 4

Production of the Electrode Plate

The electrode plate of the invention is obtained by, for instance, compression molding a thin polyester sheet at elevated temperature. The electrode plate is made of a flexible material (e.g. thin polyester) that can adapt to different body curvatures and that is accepted for medical use. The stiffness of the electrode plate must be sufficient to cause a tension in the plate when flattening it. The stiffness can be determined by choosing a polyester sheet of appropriate thickness. As mentioned above it is an advantage if the stiffness of the electrode plate varies between different regions. For example, higher stiffness is required near the sites where the needle-like electrodes are attached to the plate than in regions required to be flexible, in particular regions located between the sites of attachment of the NL and PC electrodes to the electrode plate, such as the sloping regions between the tops or crests of the elevations and the bottom areas of the depressions. Such variations in stiffness can be provided by varying the thickness of the electrode plate accordingly, reduced thickness increasing flexibility. The electrode plate of the invention can however also be made of materials that are not only resiliently flexible, such as the aforementioned polyester plate, but also resiliently extendible or stretchable. A preferred material of this sort is polyurethane. To provide sufficient stiffness in, for instance, electrode plate portions intended for mounting the NL and/or CP electrodes, the polyurethane matrix can be provided with stiffening elements, such as glass or carbon fibers. The stiffening elements prevent extension of the matrix in the direction of their disposition.

In one embodiment, electrically conductive straps of, for instance, copper are bonded by conventional screen printing or etching techniques to a thin and flexible sheet of for example polyester for connecting the NL and CP electrodes to a multi-channel stimulator. A polymer sheet of this kind can be made from, for instance, polyester by compression molding. However, the depressions and elevations may also be produced by attaching a compression-molded flexible material with the necessary dimples and elevations to a flat, thin and flexible polyester sheet provided with conductive straps. To insulate the electrically conductive straps a thin plastic film is laid on the front face and bonded to it by, for instance, infrared heating; the polymer film must not cover the contact sites for the NL electrodes or the CP electrodes. In another but not preferred embodiment, thin wires of, for instance, copper are attached to the rear face of the electrode plate for connecting the electrodes to a stimulator. The NL electrodes can be attached to the electrically conductive straps or wires by using electrically conductive adhesive or by welding or soldering, depending on the material(s) used. The CP electrodes are preferably of the same material as the electrically conducting straps.

If resiliently stretchable areas in the electrode plate are desired, instead of choosing an appropriate material such as polyester, the compression molded sheet carrying the electrically conducting wires can be cut to produce sort of fingers. Each finger carries a number of electrically conducting straps that connect a row of NL electrodes and CP electrodes to the stimulating unit. Preferably, the fingers are joined on one side of the plate like the root of a hand where the connections to the stimulating unit are to be attached. Each finger contains a row of elevations and dimples. The stiffness of the fingers must be such that the required tension in the electrode plate is produced on flattening the fingers. To hold the fingers together a sheet of stretchable material such as polyurethane or silicon rubber is posed on the rear face of the electrode plate and bonded to it.

Example 5

Multi-Channel Stimulating Unit

The NL and CP electrodes can be addressed separately by a stimulator that provides consecutive stimulation. Such stimulators are commercially available. Due to the multi-channel design of electrode plate, any desired pattern of stimulation can be produced. The multi-channel stimulator unit should be as small as possible and connected by a multi-wire cable to the electrode plate. Re-chargeable batteries with a power sufficient for 1-3 treatments are preferred.

Example 6

Stimulation

Stimulation is produced through any of the CP or NL electrodes (usually a cathode) and a reference electrode (usually an anode). Preferably the CP electrodes are used as reference electrodes. To avoid that the current always passes through the same CP electrode, the stimulator should be programmed so as to use a majority or all CP electrodes, except the active one (i.e. the cathode), as reference electrodes (i.e. anode). For example, in one moment current will pass through one CP electrode (the cathode) and/or one NL electrode (cathode) while the rest of the plate electrodes serve as the anode. The following stimulation pulse is administered via another CP electrode as the cathode, while the other CP electrodes serve as anode, and so forth.

In a preferred embodiment, the stimulation via one CP electrode and a neighboring NL electrode is phase-locked such that the signals produced in $A\beta$ fibers will arrive at the spinal cord prior to and overlapping in time with the signals produced in slower conducting $A\delta/C$ fibers. Pairs or other combinations of CP and NL electrodes are stimulated consecutively in either a random pattern or in an orderly pattern. Various patterns are possible. For example, the NL and CP electrodes can be stimulated pair-wise in a sequence starting at one side (edge) of the electrode plate and proceeding from there to the other side, thus causing a sensation of a sweeping stimulation. This pattern mimics the sequence of input that will occur naturally when scratching or massaging the skin, and may be preferred by patients suffering from chronic itch or pain.

Figure 12:
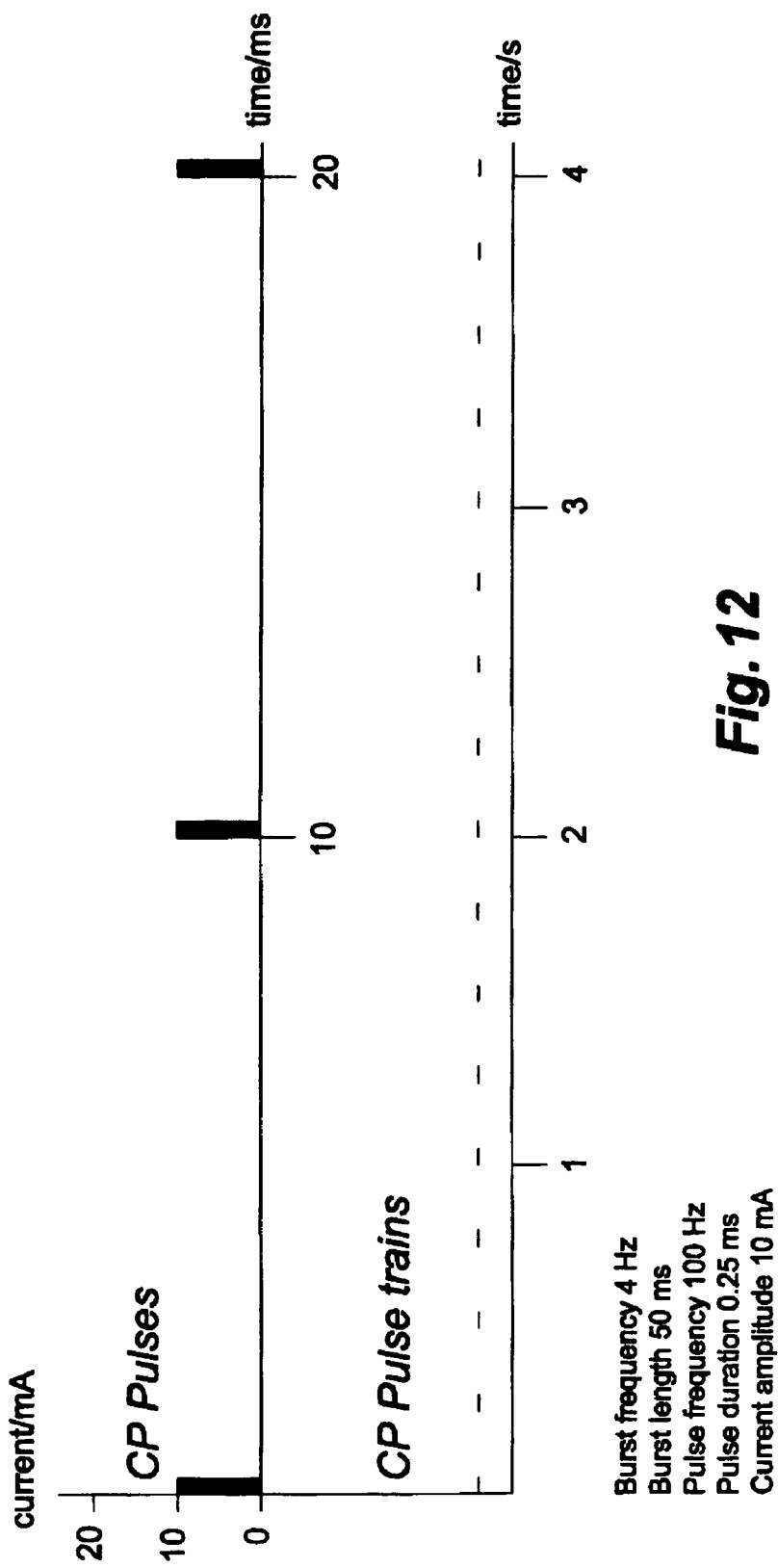
FIG. 12 is a diagram illustrating a mode of pulsing CP electrodes.

Short high frequency pulse trains (bursts) of a frequency (burst frequency) of 0.1-10 Hz are administered via CP electrodes for stimulating $A\beta$ fibers. Preferred parameters are: internal frequency, from 50 to 400 Hz; burst length per CP electrode, up to 100 ms; pulse duration, from 0.05 to 0.3 ms, more preferred 0.1-0.2 ms; current amplitude, up to 50 mA, more preferred less than 20 mA. For stimulating deep afferent fibers the current strength may have to be increased further. An example of $A\beta$ fiber stimulation is shown in FIG. 12.

Figure 13:
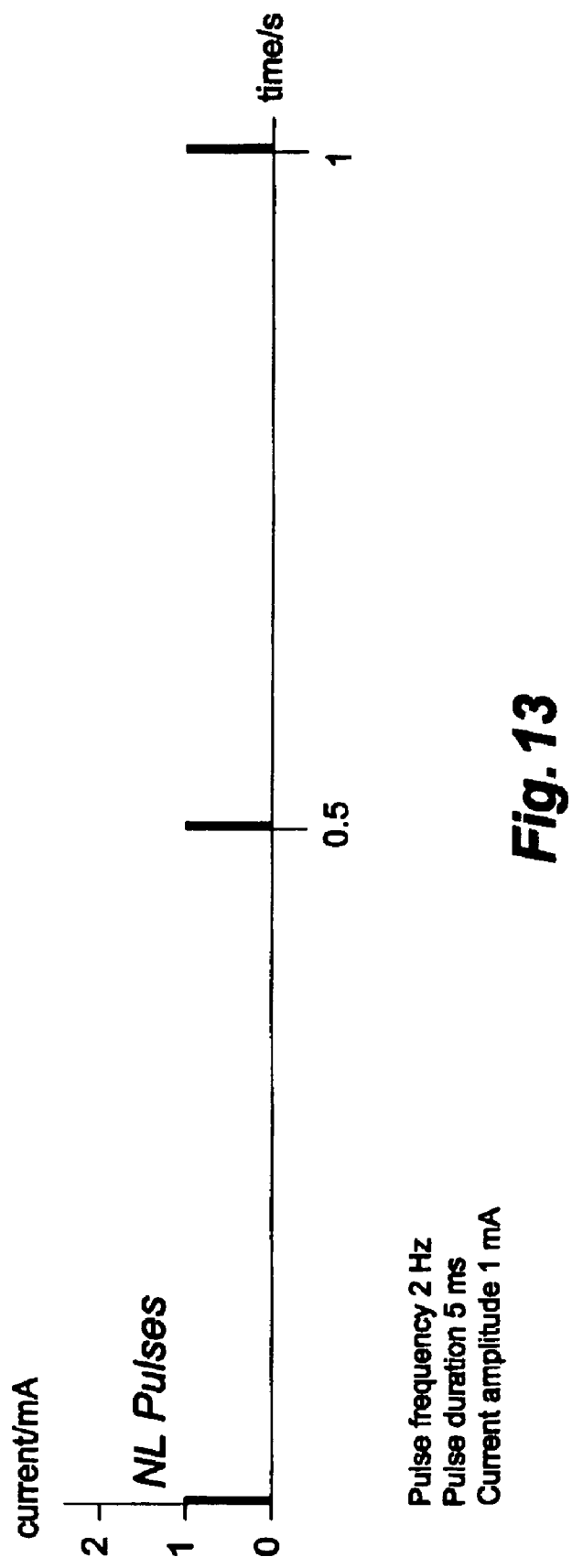
FIG. 13 is a diagram illustrating a mode of pulsing NL electrodes.

Single pulses of a frequency from 0.1 to 10 ms are administered via NL electrodes for stimulating $A\delta/C$ fibers. Preferred parameters are: pulse duration, 0.5-10.0 ms, more preferred 1.0-5.0 ms; current amplitude up to 2 mA, more preferred less than 1.2 mA. An example of $A\delta/C$ fiber stimulation is shown in FIG. 13.

To adapt the patient to the feelings produced by the stimulator, the stimulation strength is preferably increased in small steps during the first minutes of treatment. The relative strength of $A\beta$ fiber stimulation may be reduced over time as the patient adapts to the stimulation sensation. These features are therefore preferably incorporated in the program by which the multi-channel stimulator controls the electrode plate of the invention.

Example 7

Stimulation of $A\delta/C$ Fibers and $A\beta$ Fibers

An electron plate of the invention was tested on four healthy adults. The electron plate had four columns with four NL electrodes each spaced 20 mm in a rectangular array. Each NL column was flanked by a column consisting of a single CP electrode (five in total) covered with electrically conducting adhesive. The NL electrodes were made in one piece. Their active length was 0.5 mm. The electron plate was controlled by a stimulator capable of pulsing each NL and each CP column individually and consecutively.

The electrode plate was attached to the skin in the manner described above. No additional fixation means were required for holding it in perfect contact with the skin. The NL electrodes were stimulated by pulses of 1.0 ms duration, amplitude up to 1 mA, pulse frequency 2 Hz per electrode. The test persons reported a pricky feeling very similar to that of CFS. Also, a flare reaction surrounding each NL electrode was observed. Upon stimulation of the CP electrodes with 10 pulse trains each per second, internal frequency of 80 Hz, pulse amplitude of up to 20 mA, pulse duration of 0.2 ms, the test persons reported a buzzying feeling. This demonstrates that the electrode plate of the invention can be used to independently stimulate nocireceptive $A\delta/C$ fibers and tactile $A\beta$ fibers. Moreover, in all persons tested the pricking sensation produced by NL stimulation was completely masked by concomitant stimulation of neighbouring CP electrodes, abolishing the aversive feeling of NL stimulation.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

The invention claimed is:

1. An electrode plate comprising:
   an electrically non-conductive plate element having a front face and a rear face; and
   a pattern of needle-like (NL) electrodes and flat conductive plate (CP) electrodes disposed on the front face of the plate element in two or more electrode combinations, each of the two or more electrode combinations having at least one NL electrode configured to apply electrical stimulation to cutaneous thin $A\delta/C$ fibers and at least one CP electrode configured to apply electrical stimulation to cutaneous large $A\beta$ fibers, and each of the CP electrodes being physically spaced and electrically separate from any needle-like protrusions on the front face of the plate element,
   wherein the needle-like protrusions include the NL electrodes.

2. The electrode plate of claim 1, wherein the CP electrodes are arranged in close proximity to the NL electrodes in a manner so to make an average distance of two to four of the CP electrodes most closely disposed around one of the NL electrodes to that NL electrode substantially shorter than the corresponding distance of two to four of the most closely disposed neighboring NL electrodes.

3. The electrode plate of claim 1, further comprising a plurality of open venting bores communicating the front face with the rear face.

4. The electrode plate of claim 1, further comprising an electrically conductive or non-conductive adhesive disposed on portions of the front face for attaching the electrode plate to the skin.

5. The electrode plate of claim 1, wherein the NL electrodes include a base portion configured to control the depth of penetration of an oblong electrode element extending perpendicularly from the base portion.

6. The electrode plate of claim 5, wherein the oblong electrode element has a free end that is pointed.

7. The electrode plate of claim 1, further comprising at least one first electrical conductor coupled to at least one of the NL electrodes and at least one second electrical conductor coupled to at least one of the CP electrodes, the first and second electrical conductors separately connecting the at least one NL electrode and the at least one CP electrode to a multi-channel stimulator unit so the at least one NL electrode and the at least one CP electrode can be addressed separately.

8. The electrode plate of claim 7, wherein the first and second electrical conductors are attached to the front face of the plate element.

9. The electrode plate of claim 8, wherein the conductors are attached to the plate element by screen printing.

10. The electrode plate of claim 1, wherein
    the front face of the plate element is formed with raised portions and recessed portions disposed between the raised portions,
    the NL electrodes are mounted on the raised portions of the front face, and
    the CP electrodes are mounted on the recessed portions of the front face.

11. The electrode plate of claim 10, wherein the raised portions are designed to carry single NL electrodes or rows of NL electrodes.

12. The electrode plate of claim 10, wherein the recessed portions provide flexibility to the plate element.

13. The electrode plate of claim 12, wherein the recessed portions are at least one of compressible, resiliently compressible, extendable, and resiliently extendable.

14. The electrode plate of claim 10, wherein
    the raised portions are configured so the NL electrodes penetrate a patient's skin to a depth of 0.1 to 10 mm.

15. The electrode plate of claim 12, wherein at least one of electrically conductive gel and electrically conductive adhesive is disposed in the recessed portions of the plate element.

16. The electrode plate of claim 15, wherein the electrically conductive gel and/or electrically conductive adhesive is disposed in electrical contact with the CP electrodes.

17. An assembly for administration of electrical stimulation to the skin of a person comprising:
    an electrode plate comprising:
       an electrically non-conductive plate element having a front face and a rear face, and
       a pattern of needle-like (NL) electrodes and flat conductive plate (CP) electrodes disposed on the front face of the plate element in two or more electrode combinations, each of the two or more electrode combinations having at least one NL electrode configured to apply electrical stimulation to cutaneous thin $A\delta/C$ fibers and at least one CP electrode configured to apply electrical stimulation to cutaneous large $A\beta$ fibers; and
    a multi-channel stimulator unit configured to separately address the NL and CP electrodes for applying consecutive electrical stimulation to cutaneous thin $A\delta/C$ fibers via the NL electrodes and electrical stimulation to cutaneous large $A\beta$ fibers via the CP electrodes.

18. The assembly of claim 17, wherein at least one first CP electrode is controlled by the stimulator unit to function as a reference electrode for the NL electrodes while the NL electrodes apply electrical stimulation to cutaneous thin $A\delta/C$ fibers and at least one second CP electrode applies electrical stimulation to cutaneous large $A\beta$ fibers.

19. The assembly of claim 18, wherein at least two first CP electrodes are coupled as anodes in their function as reference electrodes.

20. The assembly of claim 18, wherein the stimulator is programmed to use a majority or all of the CP electrodes as first CP electrodes, except the at least one second CP electrode.

21. The assembly of claim 17, wherein one of the CP electrodes and a neighboring one of the NL electrodes are phase-locked.

22. The assembly of claim 21, wherein consecutive pairs or other combinations of CP and NL electrodes apply electrical stimulation in a random pattern.

23. The assembly of claim 21, wherein consecutive pairs or other combinations of CP and NL electrodes apply electrical stimulation in an orderly pattern.

24. The assembly of claim 17, wherein the stimulator is configured to provide current to the CP electrodes for stimulating Aβ fibers with pulse trains (bursts) having a burst frequency of from 0.1 Hz to 10 Hz; an internal frequency of from 50 Hz-400 Hz; a burst length per CP electrode of up to 100 ms; a pulse duration of from 0.05 ms to 0.3 ms; and a current amplitude of up to 50 mA.

25. The assembly of claim 17, wherein the stimulator is configured to provide current to the NL electrodes for stimulating Aδ/C fibers with single pulses of from 0.1 Hz to 10 Hz; a pulse duration of from 0.5 to 10.0 ms; and a current amplitude of up to 2 mA.

26. The electrode plate of claim 17, wherein
the pattern of NL electrodes and CP electrodes is made up of two or more rows extending across the front face of the plate element that each include two or more pairs of NL electrodes and CP electrodes, and
the multi-channel stimulator unit is configured to apply electrical stimulation to cutaneous thin Aδ/C fibers progressively from a first row to an adjacent row across the front face of the plate element.

27. The electrode plate of claim 26, wherein applying electrical stimulation to cutaneous thin Aδ/C fibers progressively from one row to an adjacent row across the front face of the plate element includes applying electrical stimulation using entire rows of NL electrode and CP electrodes.

28. The electrode plate of claim 26, wherein at least one of the two or more pairs of NL electrodes and CP electrodes in at least one row of the two or more rows shares at least one CP electrode with at least one of the two or more pairs of NL electrodes and CP electrodes in at least one adjacent row of the two or more rows.

29. The electrode plate of claim 1, wherein the at least one NL electrode in each of the two or more electrode combinations is physically spaced 1 mm to 20 mm from the at least one CP electrode in that combination on the front face of the plate element.

30. A treatment device comprising:
an electrode plate made of electrically non-conductive material having a front face and a rear face;
a plurality of needle-like (NL) electrodes disposed on the front face of the electrode plate;
a plurality of flat conductive plate (CP) electrodes disposed on the front face of the electrode plate physically spaced and electrically separate from any needle-like protrusions on the front face of the electrode plate, the needle-like protrusions including the NL electrodes; and
a stimulator for concurrently applying electrical stimulation to cutaneous large Aβ fibers via the CP electrodes and to cutaneous thin Aδ/C fibers via the NL electrodes,
wherein the plurality of NL electrodes and the plurality of CP electrodes are disposed on the front face of the electrode plate in two or more electrode combinations, each of the two or more electrode combinations having at least one NL electrode and at least one CP electrode.

31. The electrode plate of claim 30, wherein each of the two or more electrode combinations has at least one NL electrode physically spaced 1 mm to 20 mm from at least one CP electrode on the front face of the plate element.

32. A treatment device comprising:
an electrode plate made of electrically non-conductive material having a front face and a rear face;
a plurality of needle-like (NL) electrodes disposed on the front face of the electrode plate;
a plurality of flat conductive plate (CP) electrodes disposed on the front face of the electrode plate physically spaced and electrically separate from any needle-like protrusions on the front face of the electrode plate, the needle-like protrusions including the NL electrodes; and
a stimulator for concurrently administering transcutaneous electrical stimulation via the CP electrodes and intracutaneous electrical stimulation via the NL electrodes,
wherein the plurality of NL electrodes and the plurality of CP electrodes are disposed on the front face of the electrode plate in two or more electrode combinations, each of the two or more electrode combinations having at least one NL electrode and at least one CP electrode.

33. The electrode plate of claim 32, wherein each of the two or more electrode combinations has at least one NL electrode physically spaced 1 mm to 20 mm from at least one CP electrode on the front face of the plate element.

* * * * *